(12) United States Patent
Guenin

(10) Patent No.: US 7,448,939 B2
(45) Date of Patent: Nov. 11, 2008

(54) METHOD AND DEVICE FOR GRINDING CONCAVE PARTS, NOTABLY FOR MANUFACTURING PROSTHESES

(75) Inventor: Maurice Guenin, La Chaux-de-Fonds (CH)

(73) Assignee: Voumard Machines Co. SA, Hauterive (CH)

( * ) Notice: Subject to any disclaimer, the term of this patent is extended or adjusted under 35 U.S.C. 154(b) by 22 days.

(21) Appl. No.: 11/373,320

(22) Filed: Mar. 10, 2006

(65) Prior Publication Data
US 2006/0217833 A1   Sep. 28, 2006

(30) Foreign Application Priority Data
Mar. 22, 2005   (EP)   ................... 05102315

(51) Int. Cl.
*B24B 5/00* (2006.01)
(52) U.S. Cl. .......................................... 451/5; 451/61
(58) Field of Classification Search .............. 451/5, 451/61, 28, 52, 51
See application file for complete search history.

(56) References Cited

U.S. PATENT DOCUMENTS 3,812,623 A    5/1974  Kikuchi et al.
5,187,900 A    2/1993  Miwa et al.
5,277,529 A *  1/1994  Anders et al. ............... 409/131
5,425,773 A    6/1995  Boyd et al.

FOREIGN PATENT DOCUMENTS

| EP | 59169756   | 9/1984  |
|----|------------|---------|
| FR | 2 151 191 A| 4/1973  |
| FR | 2718635 A  | 10/1995 |
| GB | 152 606 A  | 1/1922  |
| GB | 2 317 584 A| 4/1998  |

* cited by examiner

*Primary Examiner*—Robert Rose
(74) *Attorney, Agent, or Firm*—Pearne & Gordon LLP

(57) ABSTRACT

Method for manufacturing cervical prostheses with a concavity after grinding, having the following steps:
  positioning a grinding tool (2) in a resting position (X0, Z0),
  loading the part (1) to grind,
  displacing the grinding tool (2) relative to the part (1) to grind along an axis (Z) parallel to the tool's rotation axis,
  displacing the grinding tool (2) relative to the part (1) to grind along an axis (X) perpendicular to the tool's rotation axis, so as to bring the tool in grinding start position,
  grinding the concavity (100) by combining rotation movements of the grinding tool and rotation movements of the part (1) around the two axes (Z, C) parallel to each other.

18 Claims, 9 Drawing Sheets

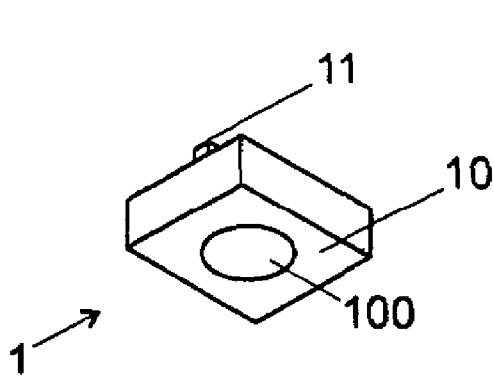
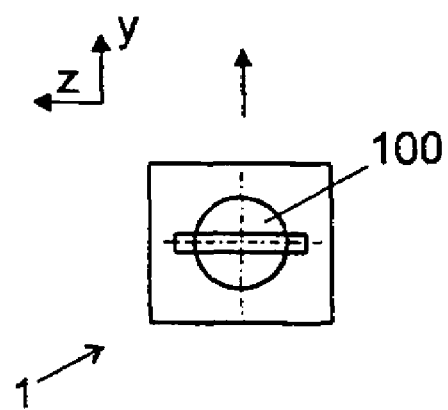
Fig. 3a                           Fig. 3b
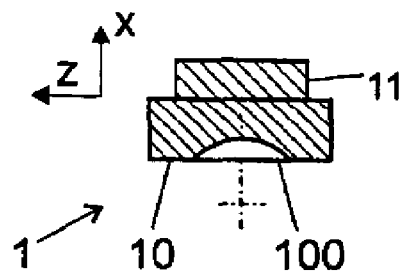
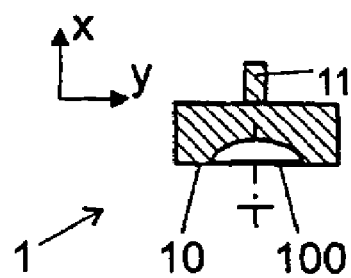
Fig. 3c                           Fig. 3d
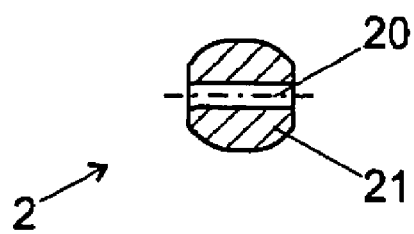
Fig. 4

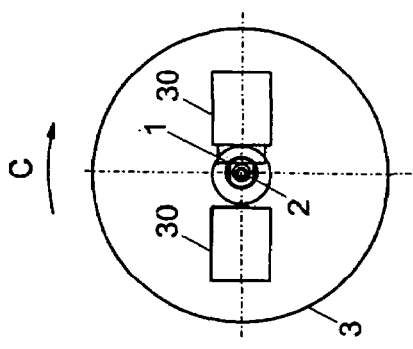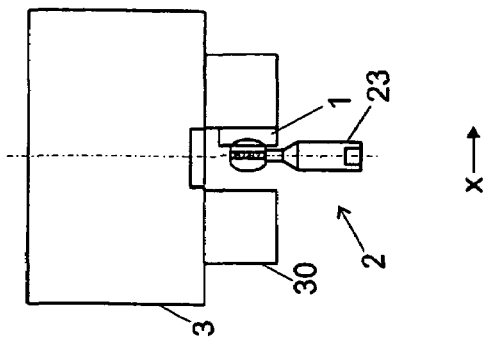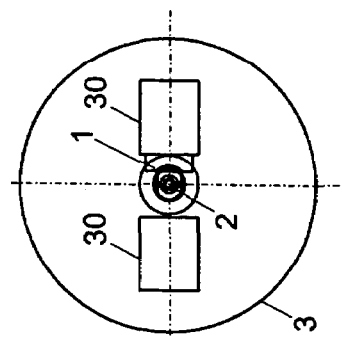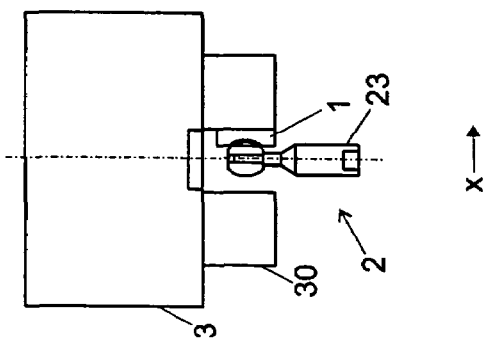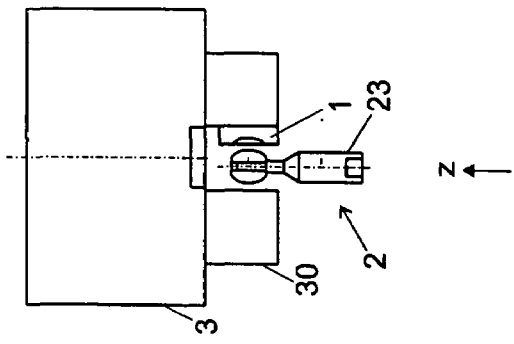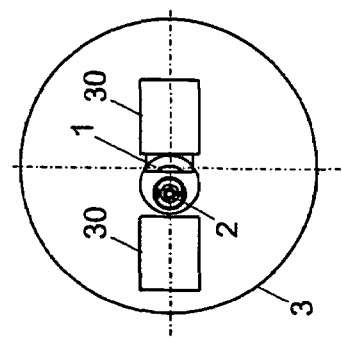

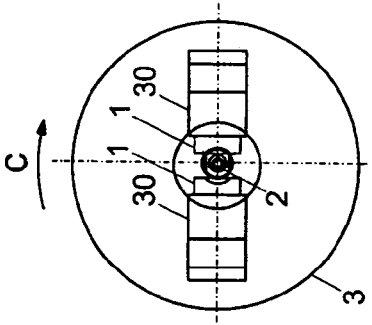
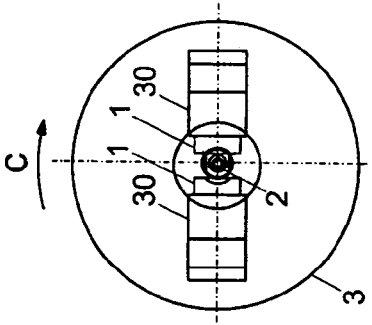
Fig. 6a  Fig. 6b  Fig. 6c  Fig. 6d
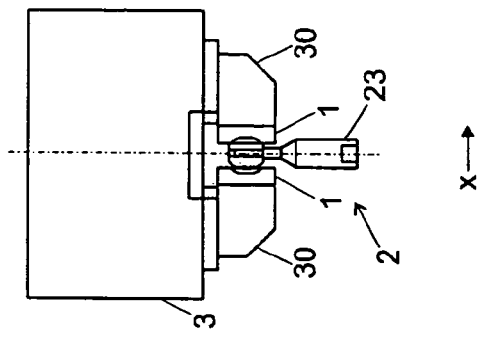
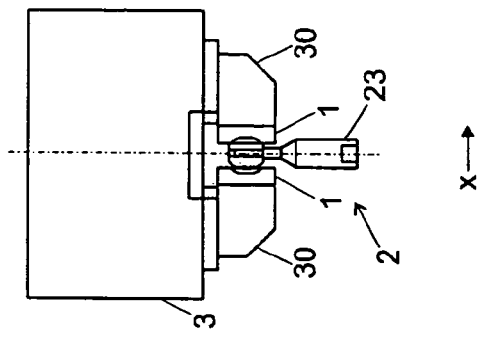
Fig. 6e  Fig. 6f  Fig. 6g  Fig. 6h

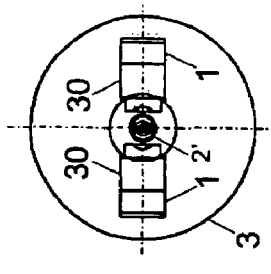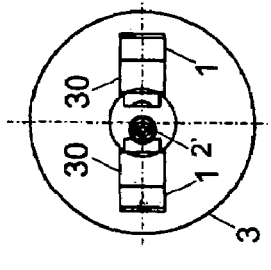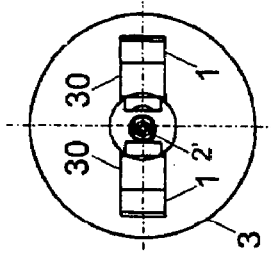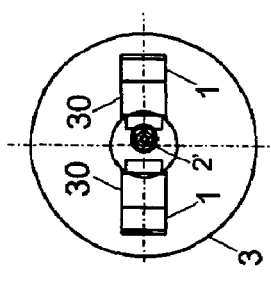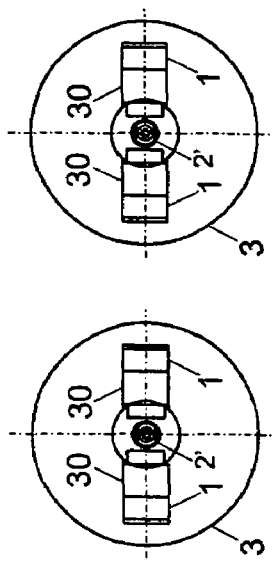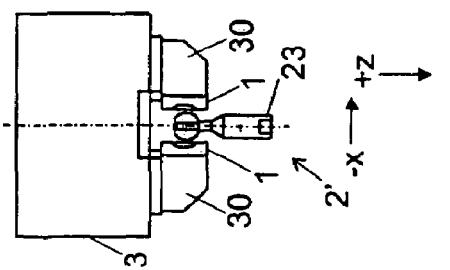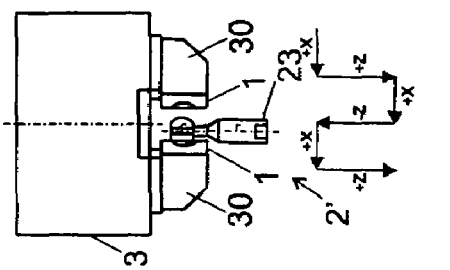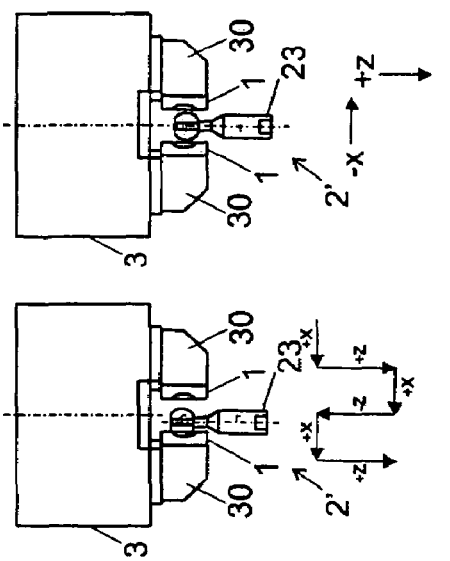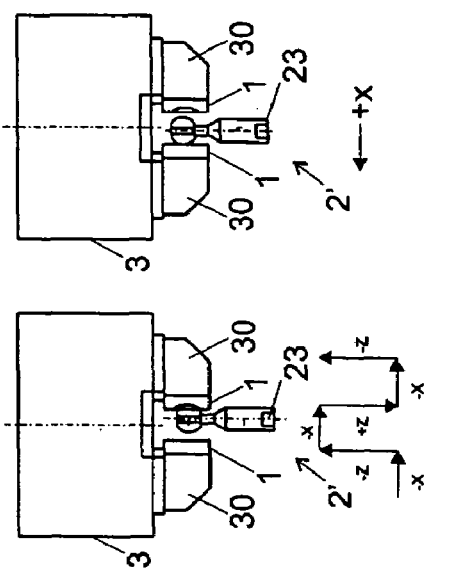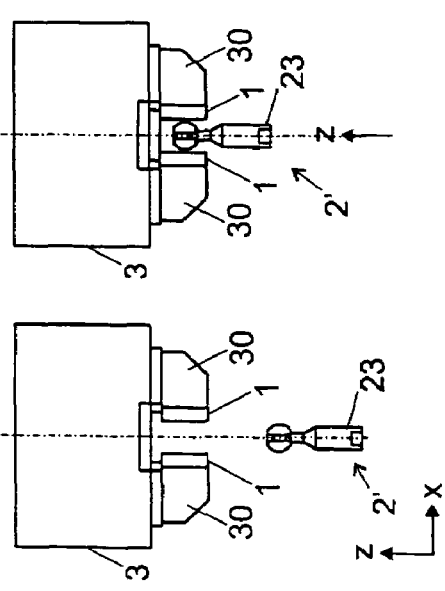

METHOD AND DEVICE FOR GRINDING CONCAVE PARTS, NOTABLY FOR MANUFACTURING PROSTHESES

REFERENCE DATA

The present application claims priority of European Patent application EP05102315, the content of which is included by reference.

TECHNICAL FIELD

The present invention concerns a method and a device for grinding concavities, notably for manufacturing cervical or other types of prostheses.

STATE OF THE ART

Cervical vertebrae and cartilaginous disks ensuring the connection between the cervical vertebrae can suffer compressions or deformations caused by shocks or repeated movements. It has already been suggested in the prior art to replace the altered vertebrae or disks with prostheses. Patent application FR2718635 describes a cervical prosthesis comprising an upper plate with a concave surface and a lower plate with a convex surface, designed to pivot in the concave surface of the upper plate. A similar prosthesis is also described in U.S. Pat. No. 5,562,738.

The surface state of the concave and convex surfaces of both plates must be perfectly smooth in order to reduce friction that would make the prosthesis sensitive to wear and would impede flexion movements. In the case of such prostheses, it is advantageous to grind the convex and concave surface after roughing out.

The present invention concerns a method and a device for manufacturing such parts, notably a method and a device for grinding the concave portion of one of the two plates.

The grinding is performed on a grinding machine with the aid of a grinding tool, for example a grinding cylinder. The grinding tool must be provided with a rod having a diameter sufficient for limiting the amplitude of the undesirable vibrations during grinding and thus achieving the required precision. It is however necessary to ensure that collisions between the tool, in particular the tool's rod, and the part to be machined be avoided.

The concave surface of the upper prosthesis advantageously has the shape of a spherical or ellipsoidal cap. The shape of the grinding tool as well as the relative movements of the tool and of the part must be adapted for grinding such a shape.

The concavities of the cervical prostheses described in the mentioned documents are not grinded, so that their quality is insufficient. Grinding methods through complex axes displacements, calling for interpolations, could also be imagined. The programming of such displacements is however complex. Considerable programming work must be undertaken in order to program the grinding of different concavities, for example to manufacture a range of prostheses for replacing different vertebrae of individuals of variable size.

One aim of the present invention is thus to propose a method and a device for grinding concavities that have been previously roughed out in one side of a part, notably of a bone prosthesis, that is simple to implement and that allows the required surface quality to be achieved.

According to the invention, these aims are achieved notably by means of a method for grinding elongated concavities previously roughed out in one side of a part, notably of a prosthesis, said concavity having a section perceptibly in the shape of a portion of circle in a plane perpendicular to the rotation axis of a tool, wherein the method includes the following steps:

positioning a grinding tool in a resting position, loading the part to grind, displacing the grinding tool relative to the part to grind along an axis parallel to the tool's rotation axis, displacing the grinding tool relative to the part along an axis (X) perpendicular to the tool's rotation axis, so as to bring the tool in grinding start position, grinding the concavity by combining the rotation movements of the grinding tool and the rotation movements of the part around the two axes parallel to each other.

The part to grind is loaded and held in a part-holding clamp bound to the chuck, itself fastened on the indexed spindle of the part-holder head (axis C). The part to grind is placed on the chuck so that the virtual center (axis) of the concavity to grind is confused with the rotation axis of the part and of the part-holder head during grinding.

This method has the advantage of allowing the grinding of concavities of variable shapes in a simple manner and with a minimum of complex displacements.

The invention will also concern a device adapted for implementing the method.

SHORT DESCRIPTION OF THE DRAWINGS

Embodiments of implementations of the invention are indicated in the description illustrated by the attached figures in which:

FIG. 3A illustrates a perspective view of a part whose lower side comprises a concavity in the shape of a spherical cap.

FIG. 3B illustrates a bottom view of the part of FIG. 3A.

FIG. 3C illustrates a side view in the direction of the axis Y of the part of FIG. 3A.

FIG. 3D illustrates a side view in the direction of the axis Z of the part of FIG. 3A.

FIG. 4 illustrates a cross-sectional longitudinal view of the abrasive part of a grinder adapted for grinding the part illustrated in FIGS. 3A to 3D.

FIGS. 5A to 5H show front views (5A-5D) and top views (5E-5H) of a device for grinding a single part per cycle, during four successive steps of a grinding cycle.

FIGS. 6A to 6H show front views (6A-6D) and top views (6E-6H) of a device for simultaneously grinding two parts per cycle, during four successive steps of a grinding cycle.

FIGS. 8A to 8L show front views (8A-8D) and top views (8E-8H) of a device for simultaneously roughing out two parts per cycle, during six successive steps of a roughing out cycle.

EMBODIMENTS OF THE INVENTION

A first embodiment of a part to grind according to the inventive method is illustrated in FIGS. 1A to 1D. The part 1 illustrated corresponds to one element of cervical or interdiscal prosthesis represented in a simplified manner. It is preferably made of metal, for example of surgical steel, titanium or ceramics. Its upper side is provided with fastening means 11 for fastening it onto the patient's organism, for example a pin designed to be cemented onto a healthy bone. The lower side 10 is provided with a concavity 100, or alveolus, in which a cervical vertebra or prosthesis can pivot and move with minimal friction.

Figure 1A:
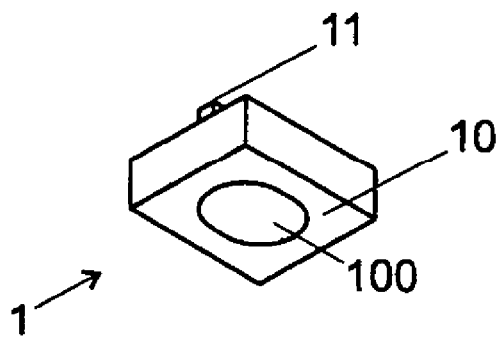
FIG. 1A illustrates a perspective view of a part whose lower side comprises a concavity in the shape of an ellipsoid cap.
Figure 1B:
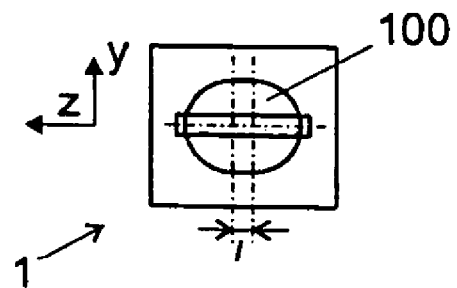
FIG. 1B illustrates a bottom view of the part of FIG. 1A.
Figure 1C:
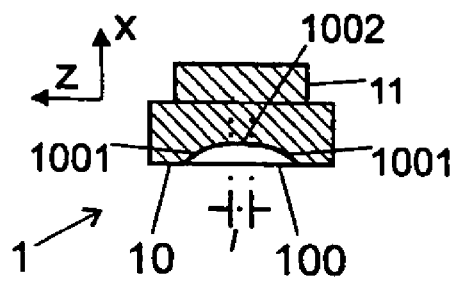
FIG. 1C illustrates a side view in the direction of the axis Y of the part of FIG. 1A.
Figure 1D:
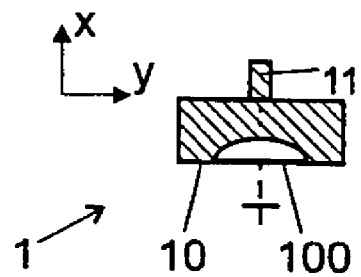
FIG. 1D illustrates a side view in the direction of the axis Z of the part of FIG. 1A.

The concavity of the FIGS. 1A to 1D has perceptibly the shape of an elongated spherical pan ("bathtub") or more generally of an ellipsoid cap; the edge of the cap, illustrated in FIG. 1B is thus at least approximately in the shape of an ellipse or oval. The section of the ellipsoid in the plane X, Z, illustrated in FIG. 1C, is at least approximately oval or elliptical. The edge 1001 has for example the shape of a segment of circle whilst the bottom 1002 is preferably cylindrical. In the plane X, Y illustrated in FIG. 1D, the cap on the other hand has a perceptibly circular cross-section. This concavity thus allows the convex element of the associated prosthesis portion to move along the axis Z and to be better held along the axis Y.

Figure 2:
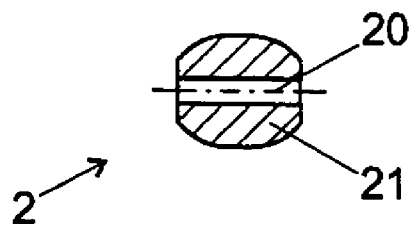
FIG. 2 illustrates a cross-sectional longitudinal view of the abrasive part of a grinder adapted for grinding the part illustrated in FIGS. 1A to 1D.
Figure 11:
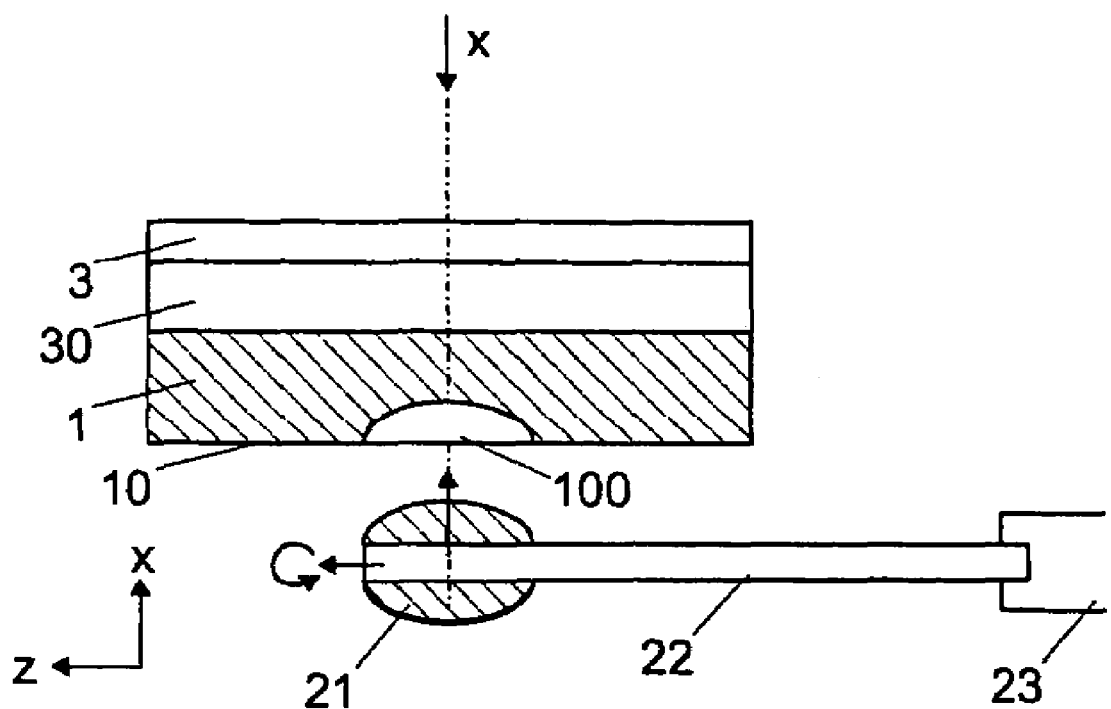
FIG. 11 illustrates a cross-sectional view along the plane (X-Z) of a part ready for grinding.
Figure 12:
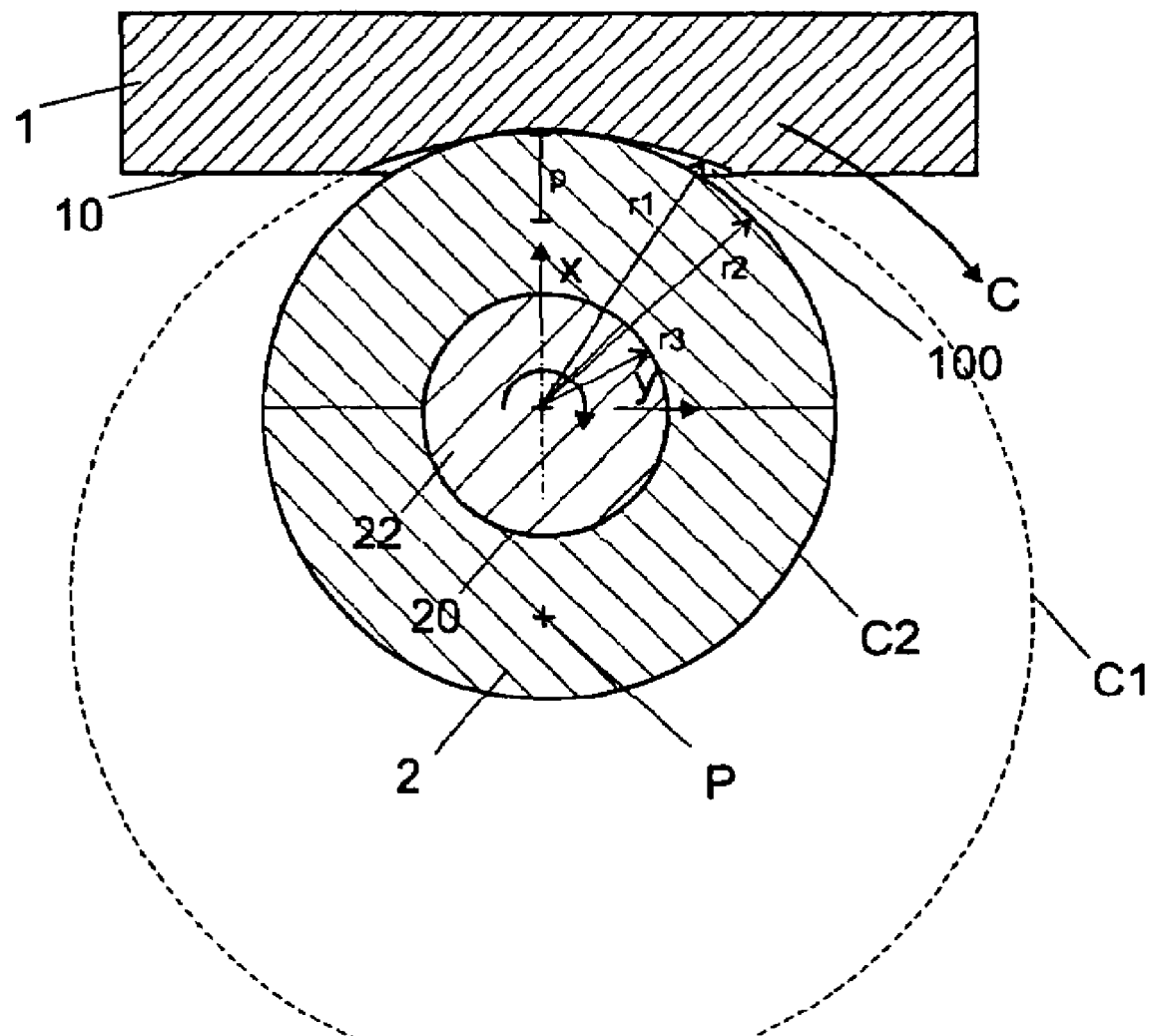
FIG. 12 illustrates a cross-sectional view along the plane (X-Y) of a part during grinding.

FIG. 2 shows an example of grinding tool suited for grinding the concavity 100 of the part illustrated in FIGS. 1A to 1D. The tool comprises an abrasive part 21 in ellipsoid shape corresponding to the shape of the concavity 100. FIG. 12 is a cross-sectional view in the plane X, Y of the tool 2 partially engaged in the concavity 100. The tool's cross-section in this plane is spherical, but its radius r2 is smaller than the curve radius r1 of the concavity in the same plane. The tool further comprises a hole 20 for mounting it on a rod 22 allowing the tool to be loaded onto a grinding holder 23 (FIG. 11) of the grinding machine. The diameter of the opening 20 and of the rod 22 is preferably as large as possible in order to hold the tool firmly whilst avoiding the risk of collision between the rod 22 and the side to be machined 10.

It is also possible to grind the concavity 100 illustrated in FIGS. 1A to 1D with the grinder having the spherical profile illustrated in FIG. 4; in this case, a displacement in z of the grinding tool 2 relatively to the part 1 is necessary.

The variant part illustrated in FIGS. 3B to 3D is similar to the variant of the parts 1B to 1D, but the concavity 100 has the shape of a spherical cap; the edge of the concavity in the plane Y-Z, illustrated in FIG. 3B, is thus circular. It is possible to grind this concavity with the grinding tool of FIG. 4, whose abrasive external surface integrates within a sphere.

The shapes of the grinding tools of FIGS. 2 and 4 can be obtained by dressing with a diamond-holder with an angular displacement that is controlled digitally. The elongated grinding tool of FIG. 2 will be dressed in three continuous steps (dressing the first part of the radius, then displacement in z by the length l, then dressing the end of the radius). The grinding tool of FIG. 4 can be dressed in a single step. The external diameter of the grinding tool diminishes after each dressing, but the profile of the abrasive portion of the grinding tool in the plane x-z preferably remains constant.

In one embodiment, the grinding tools can be dressed with the aid of a diamond dresser-cutter by interpolation x and z, in order to obtain the respective grinding tool shapes of FIGS. 2 and 4.

Figure 9:
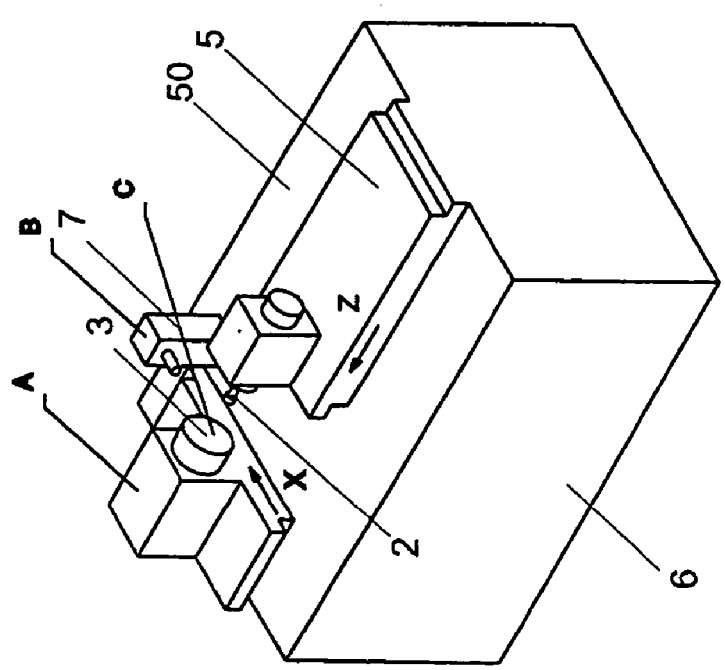
FIG. 9 illustrates in perspective, in a simplified diagrammatic manner, a first embodiment of the grinding machine capable of implementing the inventive method.

One example of grinding machine that can be programmed for executing the inventive method is illustrated diagrammatically in FIG. 9. The machine comprises a frame 6 onto which a table 5 is mounted that allows a slider 50 to move along a horizontal axis Z. A grinding tool 2 is mounted with the aid of a grinding spindle (not illustrated) on the slider 50, and can turn by means of a motor around an axis parallel to Z.

The part to grind is held in the clamp of a chuck on the head 3 capable of turning along an axis C parallel to the horizontal axis Z. The head 3 can further be displaced relatively to the frame 6 along a horizontal axis X perpendicular to the axis Z. The machine can further comprise dressing elements 7.

Figure 10:
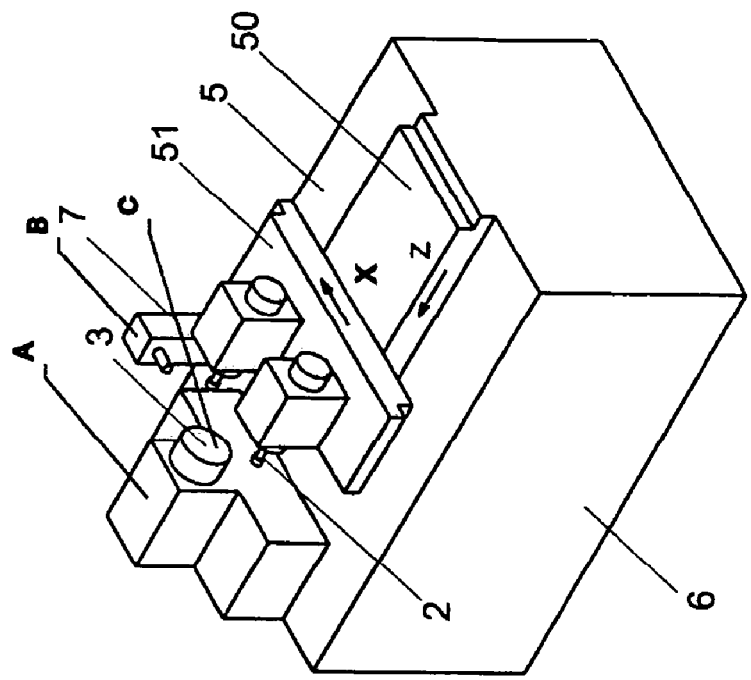
FIG. 10 illustrates in perspective, in a simplified diagrammatic manner, a second embodiment of the grinding machine capable of implementing the inventive method.

A more complex variant of grinding machine is illustrated in FIG. 10. This machine includes, in addition to the elements already present on the machine of FIG. 9, a second slider 51 on the table 5 in order to move the tools along the axis X instead of moving the head 3. This machine further comprises two parallel grinding spindles driven independently from one another.

Other configurations of grinding machines allowing at least the part and the tool to be displaced relatively to one another along the axes X, Z and C can also be conceived within the frame of the invention.

FIGS. 5E to 5H show front views (5A-5D) and top views (5E-5H) of a device for grinding a single part per cycle, during four successive steps of a cycle. In this embodiment, the linear displacements of the grinding tool 2 relatively to the part 1 are performed by movements of the table 5 holding the tool 2 along the horizontal axes X and Z; the movements along X and/or Z could however also be achieved by moving the part. The part 1 can further turn around a horizontal axis C. The axis C is parallel to but distinct from the tool's rotation axis; the displacements along X allow these two axes to be moved apart or closer.

In the position illustrated in FIGS. 5A and 5E, the part to grind, previously roughed out, has already been loaded in the clamp of the chuck 30. The tool 2 is in a resting position X0, Z0 without risk of collision with the part 1. The chuck is indexed in a predefined position along the axis C. This position allows the tool, for example a grinder, to engage inside the concavity whilst avoiding any risk of collision.

In FIGS. 5B and 5F, the tool is moved along the axis Z towards a position opposite and at a distance to the concavity 100. The chuck is always indexed. This position is illustrated enlarged in FIG. 11.

In FIGS. 5C and 5G, the tool is moved along the axis X only into grinding start position. The tool's abrasive part is then partially engaged in the concavity 100, in the position illustrated in FIG. 12.

The chuck 30 holding the part 1 is made to rotate along the axis C in the position illustrated in FIGS. 5D and 5H. The grinding begins and combines the rotations of the part along the axis C with the displacements of the tool along the axis X (quick approach, then indenting) in order to perform the finishing and then the superfinishing of the concavity.

Once the grinding has been completed, the tool is disengaged in grinding start position, the chuck is stopped and then indexed, then the tool is completely disengaged in position X0 and finally removed in position Z0. The part after grinding can then be discharged in order to begin a new cycle with a new part.

FIGS. 6A and 6H show front views (6A-6D) and top views (6E-6H) of a machine whose chuck 30 has two clamps (not represented) placed each on a shuttle for the simultaneous grinding of two parts 1 opposite one another during the same cycle. The two shuttles can be in open position towards the outside of the chuck, for loading, or closed towards the center of the chuck during grinding. In closed position, the positions of the shuttles are such that the virtual centers of the profiles after grinding are confused with the chuck's axis. The grinding tool's entering into and exiting from the concavities can occur only when the shuttles are in open position.

In FIGS. 6A and 6E, the two parts have been loaded in their respective clamps, and the tool 2 is offset in position X0, Z0. X0 corresponds to the center of the part-holder head 3. The chuck is indexed.

In FIGS. 6B and 6F, the chuck is always motionless and indexed, the tool is brought forward along the axis Z opposite the two concavities, centered relatively to the head. The jaws then close in the position illustrated in FIGS. 6C and 6G, which amounts to moving the two parts 1 in the same direction X and in an opposite sense, so as to move them closer to the tool 2. The abrasive portion of the tool is then partially engaged in the two concavities 100 of both parts, in grinding start position.

The chuck is then made to rotate along the axis C, which allows the grinding illustrated in FIGS. 6D and 6H to begin. The grinding combines quick approaches along the axis X, through displacement of the tool 2, and indenting along X, so as to perform a finishing and then a superfinishing of the part.

After grinding, the tool returns in the position X0 at the center of the spindle, the chuck is stopped and indexed, then the jaws are opened to allow the tool to disengage along the axis Z until the initial position Z0. The parts after grinding can then be discharged in order to begin a new cycle with new parts.

Depending on the geometry of the parts to be machined, and by possibly performing additional axes displacements, it is also possible within the frame of the invention to machine simultaneously more than two parts during one cycle and by using the same tool.

As can be seen in particular in FIG. 12, the grinding tool 2 turns around the axis Z and the part turns around the second axis C distinct from Z. The axis C passes through the virtual center P of the profile, i.e. through the center of the circle C1 defining the concavity 100 in the plane of the page. Furthermore, the radius r2 of the circular section of the tool 2 in the plane X, Y is considerably smaller than the radius r1 of the concavity 100. In this context, considerably smaller means that the difference is neither due to chance nor to the necessary play, but that the difference is intentional and allows a rotation of the tool relatively to the part along the axis C.

The shape and size of the concavity depends thus both on the shape of the grinding tool and on the trajectory traveled by the part around the grinding tool.

In order to avoid collisions, it is important that the difference between the maximum radius r2 of the abrasive portion 21 and the radius r3 of the rod 22 be greater than the maximum depth p of the concavity 100. One will however preferably chose a rod of a maximum diameter fulfilling this condition, taking into account a security margin in order to avoid collisions due to manufacturing tolerances and to deformations of the tool and/or of the part during grinding.

FIGS. 7A to 7H illustrate the operations performed to roughen out the concavity 100 in a part previously machined on a conventional machine-tool. The roughing out can be performed on the grinding machine described higher, by replacing the grinding tool 2 by a roughing out tool 2', or on another machine performing only the roughing out and allowing displacements along the same axes. In a preferred embodiment, the roughing out and the grinding are both performed on a single machine having two machining spindles, as illustrated in FIG. 10, one of the spindles being provided with a roughing out tool 2', for example a milling cutter or a spherical galvanic mill, the other spindle being provided with a grinding tool 2, for example a grinder.

Figure 7D:
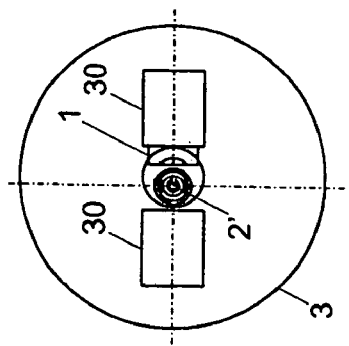
FIGS. 7A to 7H show front views (7A-7D) and top views (7E-7H) of a device for roughing out a part, during four successive steps of a roughing out cycle.
Figure 7C:
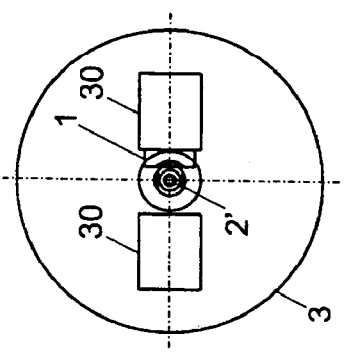
Figure 7B:
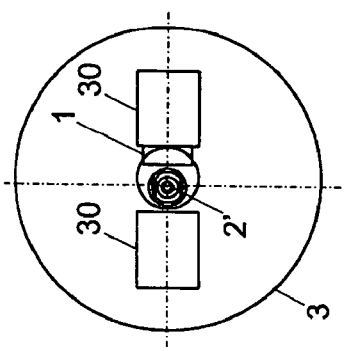
Figure 7A:
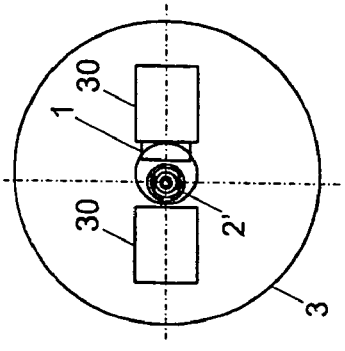
Figure 7H:
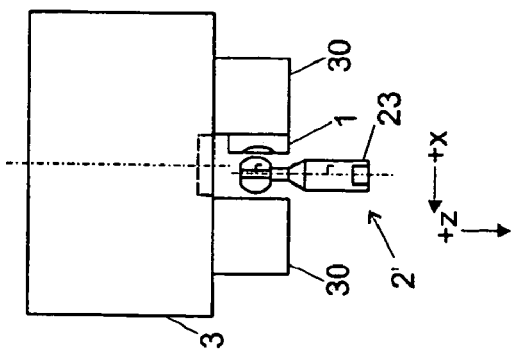
Figure 7G:
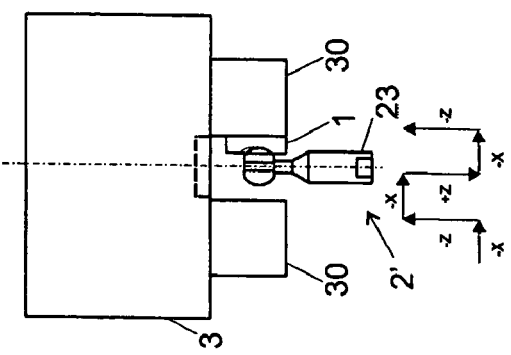
Figure 7F:
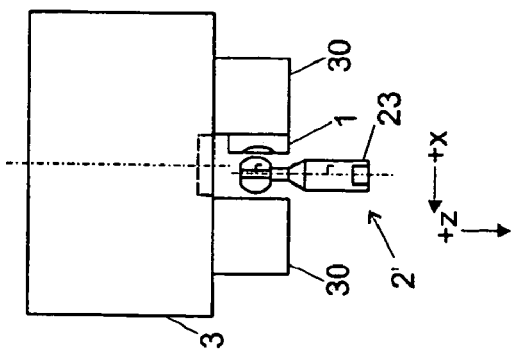
Figure 7E:
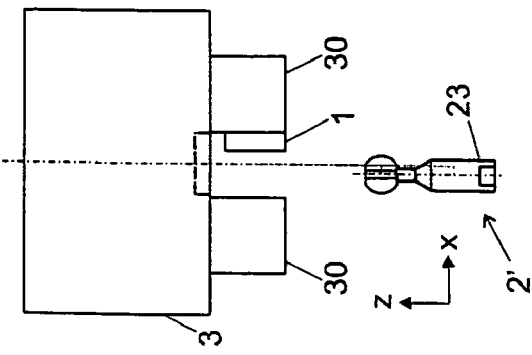

On FIGS. 7A and 7E, the part 1 is loaded, the chuck is indexed, the tool 2' is in resting position X0, Z0. The tool is then displaced along the axis Z in the position illustrated in FIGS. 7B and 7F opposite the concavity to be machined.

The machining of the concavity 100 is performed on FIGS. 7C and 7G by a combination of advances along X and Z, with the chuck 3 always remaining indexed and being not put into rotation. After roughing out, the tool 2' is disengaged by a first backwards movement along the axis X, then by a second backward movement along the axis Z (FIGS. 7D-7H) so as to return to the initial position X0Z0 allowing the part to be discharged (if necessary) or displaced along the axis X opposite the grinding tool on the same machine.

The FIGS. 8A to 8L illustrate the operations performed for roughing out the concavity 100 with the aid of a machine allowing several parts to be roughened out during the same cycle.

As for the embodiment of FIG. 7, the roughing out is advantageously, though not necessarily, performed on the machine that also performs the grinding and provided both with a roughing out spindle and a grinding spindle.

In the FIGS. 8A and 8G, the part 1 is loaded, the chuck is indexed, the tool 2' is in resting position X0, Z0. The tool is then moved along the axis Z, in the position illustrated in FIGS. 8B and 8H, opposite the two concavities to be machined in the two parts opposite 1.

The machining of the concavity 100 in the first part (on the right of the tool in the figure) is performed on the FIGS. 8C and 8I by displacing the tool 2' towards this first part and/or by closing the jaw holding this first part. The roughing out is performed by a combination of moves forward along X and Z, with the chuck 3 always remaining indexed and not being made to rotate.

After roughing out of the first part, the roughing out tool 2' is then disengaged in position X0 (FIGS. 8D and 8J), then moved closer to the second part (on its left on the figures) by displacing the tool along the axis X and/or by closing the jaw holding the second part. The machining of the second concavity is then performed by combining the displacements along X and Z, with the chuck remaining motionless, as illustrated in FIGS. 8E and 8K.

After roughing out of the concavities on the two parts, the tool 2' is disengaged by a first backwards movement along the axis X, then a second backwards movement along the axis Z, so as to return to the initial position X0Z0 allowing the part to be discharged (if necessary) or displaced along the axis X opposite the grinding tool on the same machine (FIGS. 8F-8L).

The roughing out and grinding machine can also be used for performing other machining operations on the same part 1, for example for roughing out and/or grinding other concave or convex portions on the side 10 of the part, for grinding the side 10, etc. These additional operations can be performed with the same tools, or with tools different from those used in the operations described further above.

LIST OF ELEMENTS

1 Part to grind
10 Side of the part comprising a concavity
100 Concavity
1001 Rounded edge of the concavity
1002 Cylindrical bottom of the concavity
11 Fastening means to the organism
2 Grinding tool (grinder)
20 Fastening hole of the rod
21 Abrasive portion
22 Rod
23 Grinding spindle
3 Part-holder head
30 Part-holder chuck
5 Table
50 Slider Z
51 Slider X
6 Frame
7 Dressing means
R1 Curving radius of the concavity in the plane X,Y
R2 Curving radius of the grinding tool in the plane X,Y

The invention claimed is:

1. A method for grinding elongated concavities previously roughed out in one side of a part, said concavity having a section perceptibly in the shape of a portion of circle in a plane perpendicular to a rotation axis of a grinding tool, wherein the method includes the following steps:
    positioning the grinding tool in a resting position, loading the part to grind,
    displacing the grinding tool relative to the part to grind along a parallel axis that is parallel to the tool's said rotation axis,
    displacing the grinding tool relative to the part to grind along a perpendicular axis that is perpendicular to the tool's rotation axis, so as to bring the tool in grinding start position, and
    grinding the concavity by combining rotation movements of the grinding tool and rotation movements of the part around said rotation axis and said parallel axis.

2. The method of claim 1, wherein said rotation axis is perceptibly parallel to said side.

3. The method of claim 1, wherein said tool is oriented parallel to the maximum elongation direction of said concavity.

4. The method of claim 1, wherein said concavity has a progressively variable depth in the concavity's elongation direction.

5. The method of claim 1, wherein the grinding tool turns around a first axis and the part turns around a second axis distinct from the first axis.

6. The method of claim 5, wherein the second axis is further removed from the machined part than the first axis.

7. The method of claim 1, wherein grinding of the concavity is performed by combining rotation movements of the grinding tool and rotation movements of the part around said rotation axis and said parallel axis, and the displacement movements of the tool relatively to the part to grind along said perpendicular axis.

8. The method of claim 4, the grinding of said part being performed by means of a tool comprising a rod and an abrasive portion at the end of the rod, the difference between the maximum radius of said abrasive portion and the radius of said rod being greater than the maximum depth of said concavity.

9. The method of claim 1, said concavity having perceptibly the shape of an ellipsoid cap with an approximately oval or elliptic section in a plane parallel to the tool's rotation axis.

10. The method of claim 9, said abrasive portion of the tool having perceptibly the shape of an ellipsoid with an approximately oval or elliptic section in a plane parallel to the tool's rotation axis and a perceptibly circular section in a plane perpendicular to the rotation axis of the tool, the radius of said section in the shape of a circular portion of the tool being considerably smaller than the radius of said section in the shape of a circular portion of the concavity.

11. The method of claim 1, wherein the rotation axis of the part during grinding goes through the virtual center of the concavity to grind.

12. The method of claim 1, wherein grinding of two parts opposite one another is performed during the same cycle by the same tool.

13. The method of claim 12, wherein said step of displacing the grinding tool relatively to the part along an axis perpendicular to the tool's rotation axis is performed by moving simultaneously said two parts in identical directions in an opposite sense, so as to move them closer to one another and to the tool, then by moving the tool towards one of the two parts.

14. The method of claim 1, including a preliminary step of machining said part and then roughing out said concavity in said part.

15. The method of claim 1, including a preliminary step of roughing out said concavity in said part, said roughing out being performed by a combination of displacements along an axis parallel to the rotation axis of the roughing out tool and of displacements along an axis perpendicular to the rotation axis of the roughing out tool, the part being motionless during roughing out.

16. The method of claim 14, said roughing out and said grinding being performed on a same machine provided with two machining spindles.

17. The method of claim 14, wherein two parts opposite one another are roughed out during the same cycle by the same tool.

18. The method of claim 1, wherein said part includes a prosthesis.

* * * * *